United States Patent
Sale et al.

(10) Patent No.: US 11,702,435 B2
(45) Date of Patent: Jul. 18, 2023

(54) BISPHOSPHITE LIGANDS BASED ON BENZOPINACOL

(71) Applicant: EVONIK OPERATIONS GMBH, Essen (DE)

(72) Inventors: Anna Chiara Sale, Recklinghausen (DE); Robert Franke, Marl (DE); Alexander Brächer, Haltern am See (DE); Dirk Fridag, Haltern am See (DE); Ana Markovic, Haltern am See (DE); Peter Kucmierczyk, Herne (DE); Johannes Knossalla, Gahlen (DE); Detlef Selent, Rostock (DE); Amin Börner, Rostock (DE); Kerstin Romeike, Rostock (DE)

(73) Assignee: EVONIK OPERATIONS GMBH, Essen (DE)

( * ) Notice: Subject to any disclaimer, the term of this patent is extended or adjusted under 35 U.S.C. 154(b) by 0 days.

(21) Appl. No.: 17/696,031

(22) Filed: Mar. 16, 2022

(65) Prior Publication Data
US 2022/0298188 A1   Sep. 22, 2022

(30) Foreign Application Priority Data
Mar. 18, 2021 (EP) .................................... 21163474

(51) Int. Cl.
  *C07F 9/6574* (2006.01)
  *C07C 45/50* (2006.01)
(52) U.S. Cl.
  CPC .................. *C07F 9/65746* (2013.01)
(58) Field of Classification Search
  CPC ......................... C07F 9/65746; C07C 45/50
  See application file for complete search history.

(56) References Cited

U.S. PATENT DOCUMENTS

| 7,615,645 | B2 | 11/2009 | Volland et al. |
| 8,003,816 | B2 | 8/2011 | Selent |
| 9,982,001 | B2 | 5/2018 | Dyballa et al. |
| 2016/0159837 | A1 | 6/2016 | Dyballa et al. |

FOREIGN PATENT DOCUMENTS

| EP | 3 029 044 A1 | 6/2016 |
| WO | 2005/042458 A2 | 5/2005 |
| WO | 2008/071508 A1 | 6/2008 |

OTHER PUBLICATIONS

U.S. Appl. No. 17/696,038, Sale et al., filed Mar. 16, 2022.
U.S. Appl. No. 17/696,125, Sale et al., filed Mar. 16, 2022.
European Search Report dated Aug. 20, 2021 for European Patent Application No. 21163474.6 (7 pages in German with Machine Translation).

*Primary Examiner* — Sikarl A Witherspoon
(74) *Attorney, Agent, or Firm* — Smith, Gambrell & Russell, LLP

(57) ABSTRACT

Bisphosphite ligands based on benzopinacol, and the use thereof in hydroformylation.

13 Claims, No Drawings

BISPHOSPHITE LIGANDS BASED ON BENZOPINACOL

The present invention relates to bisphosphite ligands based on benzopinacol, and the use thereof in hydroformylation.

WO 2008/071508 A1 describes a process for hydroformylation using bisphosphite ligands. Inter alia, the use of the ligand (D-1) is described.

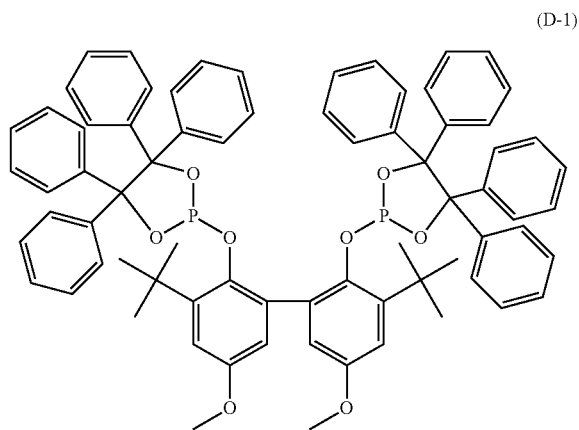 [SMILES: COc1cc(-c2cc(OC)cc(C(C)(C)C)c2OP2OC(c3ccccc3)(c3ccccc3)C(c3ccccc3)(c3ccccc3)O2)c(OP2OC(c3ccccc3)(c3ccccc3)C(c3ccccc3)(c3ccccc3)O2)c(C(C)(C)C)c1]

(D-1)

The technical problem addressed by the present invention is that of providing novel compounds which deliver increased yield in the hydroformylation of olefins compared to the compounds known from the prior art.

This problem is solved by a compound according to claim 1.

Compound of formula (I):

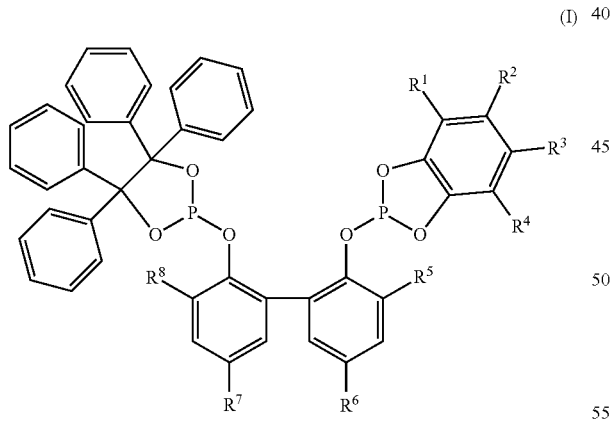

(I)

wherein $R^1$, $R^2$, $R^3$, $R^4$, $R^5$, $R^6$, $R^7$, $R^8$ are each independently selected from: —H, —($C_1$-$C_{12}$)-alkyl, —O—($C_1$-$C_{12}$)-alkyl.

The expressions —($C_1$-$C_2$)-alkyl and —O—($C_1$-$C_{12}$)-alkyl encompass straight-chain and branched alkyl groups having 1 to 12 carbon atoms. These are preferably —($C_1$-$C_6$)-alkyl groups or —O—($C_1$-$C_8$)-alkyl groups, particularly preferably —($C_1$-$C_4$)-alkyl groups or —O—($C_1$-$C_4$)-alkyl groups.

In one embodiment, $R^5$ and $R^8$ are —($C_1$-$C_{12}$)-alkyl.

In one embodiment, $R^5$ and $R^8$ are -$^{tert}$Bu.

In one embodiment, $R^6$, $R^7$ are selected from: —($C_1$-$C_{12}$)-alkyl, —O—($C_1$-$C_{12}$)-alkyl.

In one embodiment, $R^6$ and $R^7$ are —$OCH_3$ or -$^{tert}$Bu.

In one embodiment, $R^1$, $R^2$, $R^3$, $R^4$ are selected from —H, —($C_1$-$C_{12}$)-alkyl.

In one embodiment. $R^1$, $R^2$, $R^3$, $R^4$ are —H or -$^{tert}$Bu.

In one embodiment, the compound has one of the structures (1) to (6):

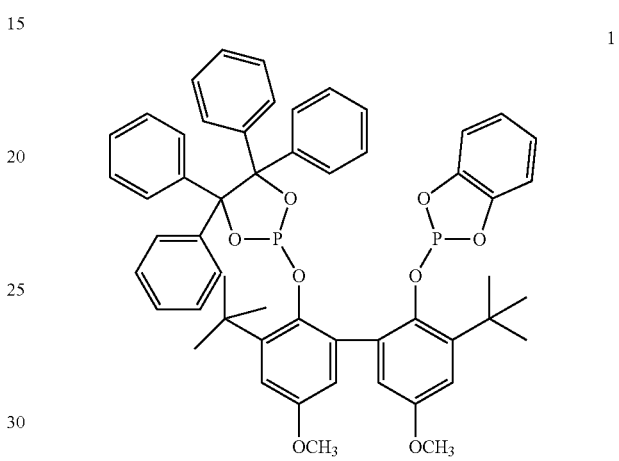

1

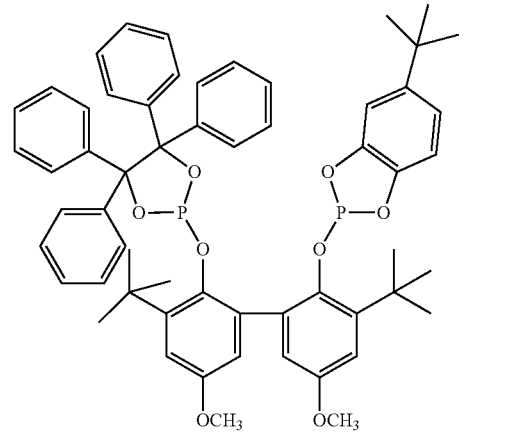

2

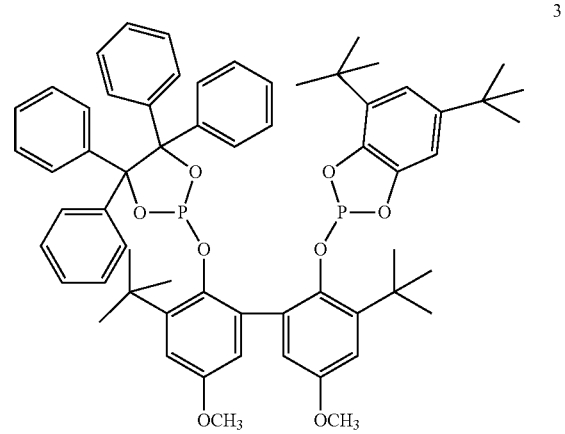 [SMILES: COc1cc(-c2cc(OC)cc(C(C)(C)C)c2OP2OC(c3ccccc3)(c3ccccc3)C(c3ccccc3)(c3ccccc3)O2)c(OP2Oc3cc(C(C)(C)C)cc(C(C)(C)C)c3O2)c(C(C)(C)C)c1]

3

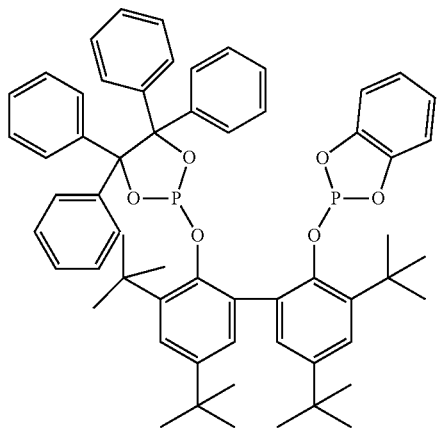

4

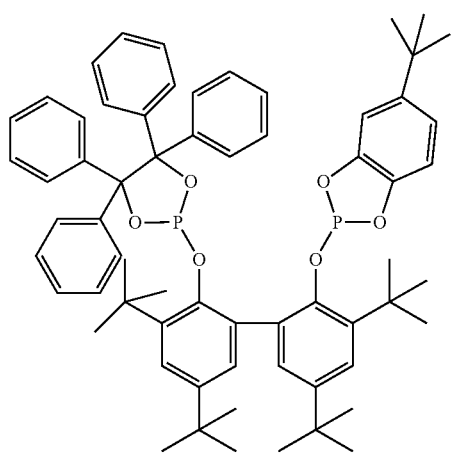

5

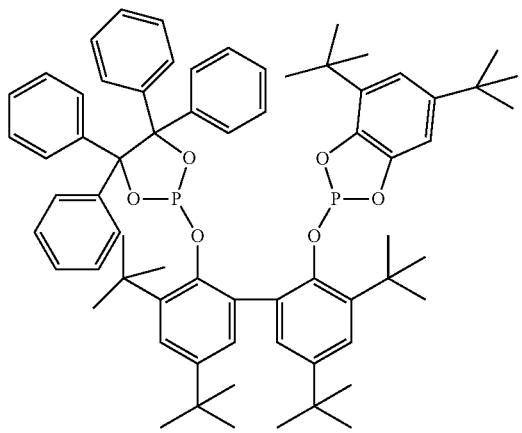

6

In addition to the compound per se, a process in which the compound is used is also claimed.

Process comprising the process steps of:
a) initially charging an ethylenically unsaturated compound;
b) adding a compound as described above and a substance comprising Rh;
c) feeding in $H_2$ and CO,
e) heating the reaction mixture from a) to c), with conversion of the ethylenically unsaturated compound to an aldehyde.

In this process, process steps a), b) and c) can be effected in any desired sequence. Typically, however, CO is added after the co-reactants have been initially charged in steps a) and b). In addition, CO can also be fed in in two or more steps, in such a way that, for example, a portion of the CO is first fed in, then the mixture is heated, and then a further portion of CO is fed in.

The ethylenically unsaturated compounds used as reactant in the process according to the invention contain one or more carbon-carbon double bonds. These compounds are also referred to hereinafter as olefins for simplification. The double bonds may be terminal or internal.

In one variant of the process, the ethylenically unsaturated compound does not comprise any further functional groups apart from carbon-carbon double bonds.

In one variant of the process, the ethylenically unsaturated compound is selected from: ethene, propene, 1-butene, cis- and/or trans-2-butene, isobutene, 1,3-butadiene, 1-pentene, cis- and/or trans-2-pentene, 2-methyl-1-butene, 3-methyl-1-butene, 2-methyl-2-butene, hexene, tetramethylethylene, heptene, 1-octene, 2-octene, di-n-butene, or mixtures thereof.

In one variant of the process, the substance comprising Rh is selected from: $Rh(acac)(CO)_2$, [(acac)Rh(COD)] (Umicore, acac=acetylacetonate anion; COD=1,5-cyclooctadiene), $Rh_4CO_{12}$.

In one variant of the process, CO is fed in in process step c) at a pressure in the range from 1 to 6 MPa (10 to 60 bar).

In one variant of the process, the reaction mixture is heated in process step d) to a temperature in the range from 80° C. to 160° C.

The invention shall be elucidated in more detail hereinbelow with reference to working examples.

Synthesis of 2-((3,3'-di-tert-butyl-5,5'-dimethoxy-d'-((4,4,5,5-tetraphenyl-1,3,2-dioxaphospholan-2-yl)oxy)-[1,1'-biphenyl]-2-yl)oxy)benzo[d][1,3,2]dioxaphosphole (1)

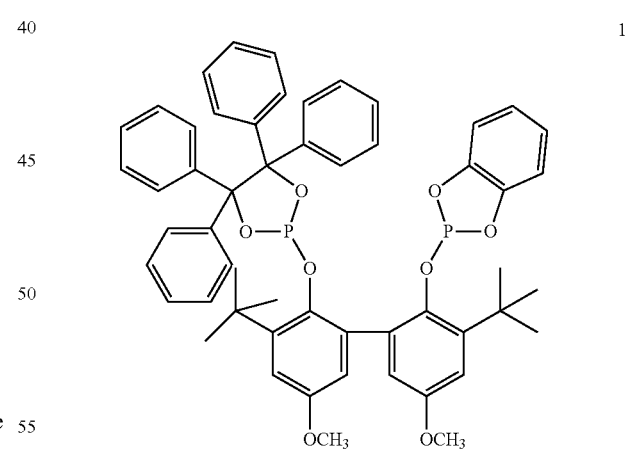

1

To a solution of 2-((3,3'-di-tert-butyl-2'-((dichlorophosphanyl)oxy)-5,5'-dimethoxy-[1,1'-biphenyl]-2-yl)oxy)-4,4,5,5-tetraphenyl-1,3,2-dioxaphospholane (0.639 g; 0.7483 mmol) in 6 ml of toluene is added dropwise, at room temperature, a mixture of catechol (0.0824 g; 0.7483 mmol) and triethylamine (0.42 ml) in 3 ml of toluene. The mixture is stirred overnight and filtered, and the filtrate is concentrated to dryness under reduced pressure. The solid obtained is dried at 60° C./0.1 mbar for 2 h and taken up in 6.5 ml of hot acetonitrile. The solid formed after cooling is filtered off, washed with a little cold acetonitrile and dried under reduced pressure. Yield: 0.426 g (0.5537 mmol, 74%).

Elemental analysis (calc. for $C_{54}H_{52}O_8P_2=890.945$ g/mol): C=72.79 (72.80); H=5.93 (5.88); P=6.98 (6.95).

ESI-TOF HRMS: m/z=891.3212; [M$^+$+H], calc. m/z=891.3215.

$^{31}$P NMR (CD$_2$Cl$_2$): d 136.0 (d, $J_{PP}$=55 Hz); 146.9 (d, $J_{PP}$=55 Hz).

$^1$H NMR (CD$_2$Cl$_2$): δ 1.29 (s, 9H); 1.35 (s, 9H); 3.74 (s, 3H); 3.80 (s, 3H); 6.75 (m, 1H); 6.82 (m, 1H); 6.95-7.16 (m, 22H); 7.32 (m, 4H) ppm.

Synthesis of 5-(tert-butyl)-2-((3,3'-di-tert-butyl-5,5'-dimethoxy-2'-((4,4,5,5-tetraphenyl-1,3,2-dioxaphospholan-2-yl)oxy)-[1,1'-biphenyl]-2-yl)oxy)benzo[d][1,3,2]dioxaphosphole (2)

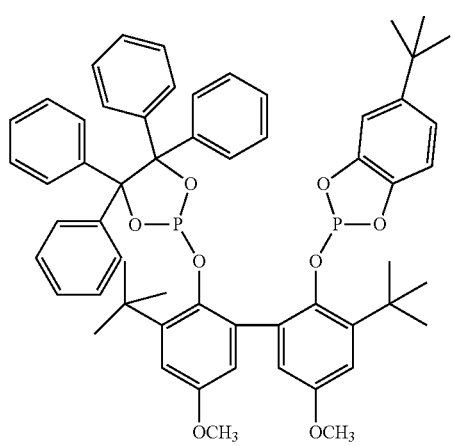

2

To a solution of 2-((3,3'-di-tert-butyl-2'-((dichlorophosphanyl)oxy)-5,5'-dimethoxy-[1,1'-biphenyl]-2-yl)oxy)-4,4,5,5-tetraphenyl-1,3,2-dioxaphospholane (0.4384 g; 0.5135 mmol) in 4 ml of toluene is added dropwise, at room temperature, a mixture of 4-tert-butylcatechol (0.0853 g; 0.5135 mmol) and triethylamine (0.29 ml) in 2 ml of toluene. The mixture is stirred overnight and filtered, and the filtrate is concentrated to dryness under reduced pressure. The solid obtained is dried at 60° C./0.1 mbar for 2 h and then taken up in 4.3 ml of hot acetonitrile.

The solid formed after cooling is filtered off, washed with a little cold acetonitrile and dried under reduced pressure. Yield: 0.201 g (0.261 mmol, 51%).

Elemental analysis (calc. for $C_{58}H_{60}O_8P_2=947.052$ g/mol): C=73.51 (73.56); H=6.63 (6.39); P=6.81 (6.54).

ESI-TOF HRMS: m/z=696.3655; [M$^+$+Na], calc. m/z=696.3660.

$^{31}$P NMR (CD$_2$Cl$_2$): d 135.7 (d, $J_{PP}$=44 Hz); 136.0 (d, $J_{PP}$=55 Hz); 145.0 (d, $J_{PP}$=55 Hz); 145.1 (d, $J_{PP}$=44 Hz) ppm.

$^1$H NMR (CD$_2$Cl$_2$): d 1.29+1.31 (2s, 9H); 1.33+1.34 (2s, 9H); 1.35 (s, 4.5H); 1.38 (s, 4.5H); 3.73 (s, 1.5H); 3.74 (s, 1.5H); 3.77 (s, 1.5H); 3.80 (s, 1.5H); 6.73 (m, 1H); 6.82 (m, 1H); 6.90-7.13 (m, 21H); 7.27-7.37 (m, 4H) ppm.

Synthesis of 4,6-di-tert-butyl-2-((3,3'-di-tert-butyl-5,5'-dimethoxy-2'-((4,4,5,5-tetraphenyl-1,3,2-dioxaphospholan-2-yl)oxy)-[1,1'-biphenyl]-2-yl)oxy)benzo[d][1,3,2]dioxaphosphole (3)

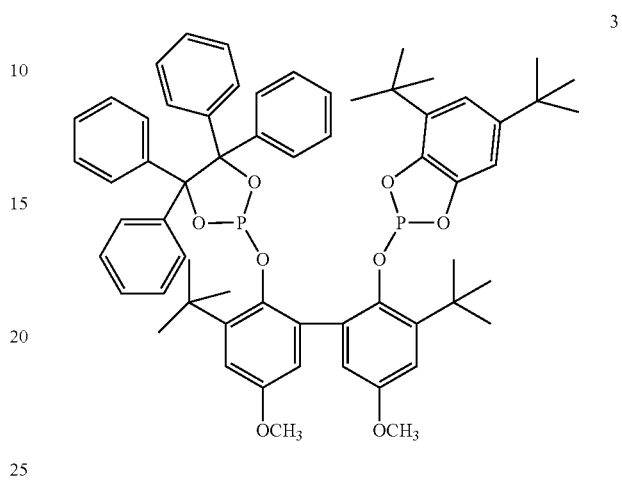

3

To a solution of L1 in 4 ml of THF is added dropwise, at −20° C., the solution of n-BuLi. The mixture is stirred for a further 20 min, then allowed to warm to room temperature, and benzopinacol phosphorochloridite, dissolved in 1.8 ml of THF, is added dropwise. The reaction mixture is stirred overnight. Triethylamine A is subsequently added and then a solution of phosphorus trichloride in 1.5 ml of THF is added dropwise to the reaction mixture cooled to 0° C. The mixture is allowed to warm to room temperature and is stirred for 6 h.

The volatile components are removed from the mixture under reduced pressure and the residue is dried at 60° C. and 0.1-0.5 mbar for 2 h. The solid obtained is taken up in 8 ml of toluene. To the resulting suspension is added, dropwise at room temperature, a mixture consisting of 3,5-di-tert-butylcatechol, triethylamine B and 3 ml of toluene. The mixture is stirred overnight, filtered (G4), the solvent is removed under reduced pressure and the solid is dried at 60° C. and 0.1-0.5 mbar. Crude yield: 1.03 g (95%).

The crude product is dissolved in 11 ml of boiling acetonitrile. The mixture is first allowed to cool slowly to room temperature and is then stored overnight at −30° C. The deposited solid is isolated, with cooling to −30° C., by siphoning off the supernatant mother liquor using an immersion frit, and is then dried under reduced pressure at 60° C. for 5 h.

Yield: 0.786 g (72%).

Elemental analysis (calc. for $C_{62}H_{66}O_8P_2=1003.16$ g/mol): C=74.24 (74.23); H=6.85 (6.83); P=6.07 (6.18).

ESI-TOF HRMS: m/z=1025.4309; [M$^+$+H], calc. m/z=1025.4287.

$^{31}$P NMR (CD$_2$Cl$_2$): d 134.1 (s, br); 134.5 (d, $J_{PP}$=77.3 Hz); 144.6 (d, $J_{PP}$=77.3 Hz); 145.2 (d, $J_{PP}$=24.7 Hz), mixture of two diastereomers.

$^1$H NMR (CD$_2$Cl$_2$): δ 1.22 (s); 1.27 (s); 1.33 (s); 1.34 (s): 1.36 (s); 1.44 (s); 1.46 (s); 1.47 (s) ppm; S=36H. 3.68 (s); 3.69 (s); 3.77 (s); 3.87 (s) ppm; S=12H. 6.59-7.43 ppm (m, 26H).

Synthesis of 2-((3,3',5,5'-tetra-tert-butyl-2'-((4,4,5,5-tetraphenyl-1,3,2-dioxaphospholan-2-yl)oxy)-[1,1'-biphenyl]-2-yl)oxy)benzo[d][1,3,2]dioxaphosphole (4)

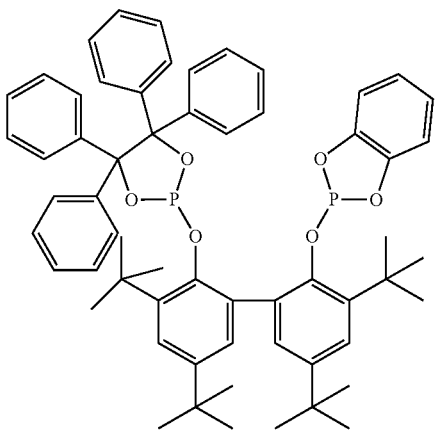

To a solution of 4,4,5,5-tetraphenyl-2-((3,3',5,5'-tetra-tert-butyl-2'-((dichlorophosphanyl)oxy)-[1,1'-biphenyl]-2-yl)oxy)-1,3,2-dioxaphospholane (0.7936 g; 0.8760 mmol) in 5 ml of toluene is added dropwise, at room temperature, a mixture of catechol (0.0964 g; 0.8760 mmol) and triethylamine (0.49 ml) in 3 ml of toluene. The mixture is stirred overnight and filtered, and the filtrate is concentrated to dryness under reduced pressure. The solid obtained is dried at 60° C./0.1 mbar for 2 h and then stirred into 7 ml of acetonitrile for 1 h. The remaining solid is filtered off, washed with a little cold acetonitrile and dried under reduced pressure. Yield: 0.6197 g (0.657 mmol, 75%).

Elemental analysis (calc. for $C_{60}H_{64}O_6P_2$=943.1076 g/mol): C=76.48 (76.41); H=6.84 (6.84); P=6.57 (6.57).

ESI-TOF HRMS: m/z=965.4076; [M$^+$+Na], calc. m/z=965.4070.

$^{31}$P NMR (CD$_2$Cl$_2$): d 134.4 (d, $J_{PP}$=13 Hz); 145.6 (d, $J_{PP}$=13 Hz) ppm.

$^1$H NMR (CD$_2$Cl$_2$): δ 1.25 (s, 9H); 1.38 (s, 9H); 1.46 (s, 9H); 1.48 (s, 9H); 6.64 (m, 2H); 6.85 (m, 1H); 6.99-7.13 (m, 19H); 7.33-7.38 (m, 3H); 7.44 (m, 1H); 7.67 (m, 2H) ppm.

Synthesis of 5-(tert-butyl)-2-((3,3'-di-tert-butyl-5,5-dimethoxy-2'-((4,4,5,5-tetraphenyl-1,3,2-dioxaphospholan-2-yl)oxy)-[1,1'-biphenyl]-2-yl)oxy)benzo[d][1,3,2]dioxaphosphole (5)

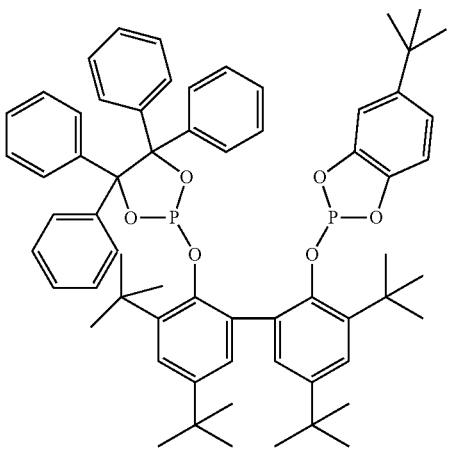

To a solution of 4,4,5,5-tetraphenyl-2-((3,3',5,5'-tetra-tert-butyl-2'-((dichlorophosphanyl)oxy)-[1,1'-biphenyl]-2-yl)oxy)-1,3,2-dioxaphospholane (0.618 g; 0.682 mmol) in 5 ml of toluene is added dropwise, at room temperature, a mixture of 4-tert-butylcatechol (0.1133 g; 0.6818 mmol) and triethylamine (0.38 ml) in 3 ml of toluene. The mixture is stirred overnight and filtered, and the filtrate is concentrated to dryness under reduced pressure. The solid obtained is dried at 60° C./0.1 mbar for 2 h and taken up in 6 ml of hot acetonitrile. The solid formed after storage of the solution in a freezer is filtered off, washed with a little cold acetonitrile and dried under reduced pressure. Yield: 0.416 g (0.477 mmol, 70%).

Elemental analysis (calc. for $C_{64}H_{72}O_6P_2$=999.215 g/mol): C=76.75 (76.93); H=7.20 (7.26); P=6.15 (6.20).

ESI-TOF HRMS: m/z=1021.4708; [M$^+$+Na], calc. m/z=1021.4696.

$^{31}$P NMR (CD$_2$Cl$_2$): d 136.2 (d, $J_{PP}$=10 Hz); 136.3 (d, $J_{PP}$=10 Hz); 145.7 (d, $J_{PP}$=10 Hz); 145.8 (d, $J_{PP}$=10 Hz) ppm. 2 diastereomers.

$^1$H NMR (CD$_2$Cl$_2$): δ 1.24+1.25 (2s, 9H); 1.35+1.37+1.38 (3s, 18H); 1.45+1.48+1.49 (3s, 18H); 6.53 (m, 2H); 6.79 (m, 1H); 6.96-7.18 (m, 18H); 7.31-7.46 (m, 4H); 7.64 (t; $J_{HH}$=2.3 Hz; 1H), 7.67 (d; $J_{HH}$=2.5 Hz; 1H) ppm.

Synthesis of 4,6-di-tert-butyl-2-((3,3',5,5'-tetra-butyl-2'-((4,4,5,5-tetraphenyl-1,3,2-dioxaphospholan-2-yl)oxy)-[1,1'-biphenyl]-2-yl)oxy)benzo[d][1,3,2]dioxaphosphole (6)

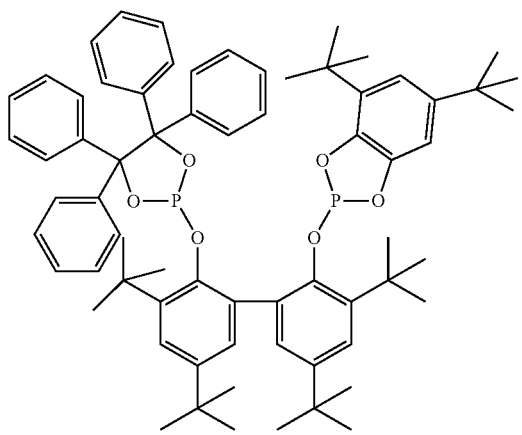

To a solution of 4,4,5,5-tetraphenyl-2-((3,3',5,5'-tetra-tert-butyl-2'-((dichlorophosphanyl)oxy)-[1,1'-biphenyl]-2-yl)oxy)-1,3,2-dioxaphospholane (0.6529 g; 0.7207 mmol) in 5 ml of toluene is added dropwise, at room temperature, a mixture of 3,5-di-tert-butylcatechol (0.1602 g; 0.7207 mmol) and triethylamine (0.40 ml) in 3 ml of toluene. The mixture is stirred overnight and filtered, and the filtrate is concentrated to dryness under reduced pressure. The solid obtained is dried at 60° C./0.1 mbar for 2 h, then stirred into 7 ml of acetonitrile for 1.5 h and dried under reduced pressure after filtration. Yield: 0.5345 g (0.5064 mmol, 70%).

Elemental analysis (calc. for $C_{66}H_{80}O_6P_2$=1055.322 g/mol): C=77.49 (77.39); H=7.57 (7.64); P=5.90 (5.87).

ESI-TOF HRMS: m/z=1077.5305; [M$^+$+Na], calc. m/z=1077.5322.

$^{31}$P NMR (CD$_2$Cl$_2$): d 132.5 (d, $J_{PP}$=20 Hz); 134.4 (s, br); 144.3 (d, $J_{PP}$=20 Hz); 145.3 (d, $J_{PP}$=11 Hz) ppm. 2 diastereomers.

$^1$H NMR (CD$_2$Cl$_2$): δ 1.19 (s; 4.5H); 1.24 (s; 4.5H); 1.31 (s; 4.5H); 1.33 (s; 4.5H); 1.34 (s; 4.5H); 1.37 (s; 4.5H); 1.41 (s; 4.5H); 1.44 (s; 4.5H); 1.45 (s, 9H); 1.47 (s; 4.5H); 1.49 (s, 4.5H); 6.42 (m, 1H); 6.73 (m; 0.5H); 6.85 (dd, $J_{HH}$=20.3 Hz; $J_{HH}$=1.99 Hz; 1H); 6.96-7.16 (m, 16H); 7.23-7.30 (m; 1.5H); 7.31-7.43 (m, 4H); 7.60 (dd, $J_{HH}$=12.5 Hz; $J_{HH}$=2.4 Hz; 1H), 7.66 (dd, $J_{HH}$=8.5 Hz; $J_{HH}$=2.5 Hz; 1H) ppm.

Catalysis Experiments

The hydroformylation was conducted in a 200 ml autoclave from Premex Reactor AG, Lengau, Switzerland, equipped with pressure-retaining valve, gas flowmeter, sparging stirrer and pressure pipette. To minimize the influence of moisture and oxygen, the toluene used as solvent was purified in a Pure Solv. MD-7 System and stored under argon. The olefin cis/trans-2-pentene used as substrate (Aldrich) was heated at reflux over sodium and distilled under argon. Toluene solutions of the catalyst precursor and of the ligand were mixed in the autoclave under an argon atmosphere. [(acac)Rh(COD)] (Umicore, acac=acetylacetonate anion; COD=1,5-cyclooctadiene) was used as catalyst precursor. The autoclave was heated with stirring (1500 rpm) at 12 bar for a final pressure of 20 bar. After reaching the reaction temperature, the olefin was injected into the autoclave by way of a positive pressure established in the pressure pipette. The reaction was conducted at a constant pressure (closed-loop pressure controller from Bronkhorst, the Netherlands) over 4 h. At the end of the reaction time, the autoclave was cooled to room temperature, depressurized while stirring and purged with argon. 1 ml of each reaction mixture was removed immediately after the stirrer had been switched off, diluted with 10 ml of pentane and analysed by gas chromatography: HP 5890 Series II plus, PONA, 50 m×0.2 mm×0.5 μm.

The reaction was conducted using compounds (1) to (6) according to the invention and using the comparative ligand (D-1).

(D-1)

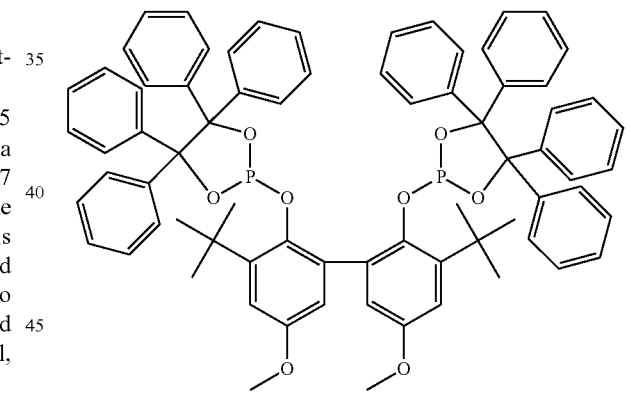

Reaction Conditions:

Olefin: 2-pentene, solvent: toluene, proportion by mass of rhodium: 100 ppm, p: 20 bar, T: 120° C., t: 4 h, Rh:ligand ratio=1:2.

The results are compiled in the following table:

| Ligand | Yield of aldehyde [%] |
|---|---|
| 1* | 99 |
| 2* | 99 |
| 3* | 99 |
| 4* | 99 |
| 5* | 99 |
| 6* | 99 |
| D-1 | 14 |

*compound according to the invention

As the experimental results show, the problem is solved by the compounds according to the invention.

The invention claimed is:

1. Compound of formula (I):

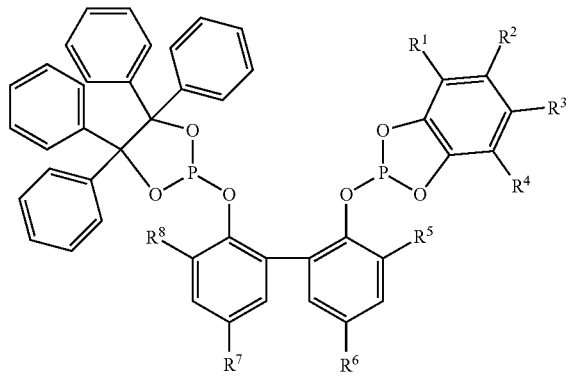

wherein
$R^1$, $R^2$, $R^3$, $R^4$, $R^5$, $R^5$, $R^7$, $R^8$ are each independently selected from: —H, —($C_1$-$C_{12}$)-alkyl, —O—($C_1$-$C_{12}$)-alkyl.

2. Compound according to claim 1, wherein $R^5$ and $R^8$ are —($C_1$-$C_{12}$)-alkyl.

3. Compound according to claim 1, wherein $R^5$ and $R^8$ are -$^{tert}$Bu.

4. Compound according to claim 1, wherein $R^5$, $R^7$ are selected from: —($C_1$-$C_{12}$)-alkyl, —O—($C_1$-$C_{12}$)-alkyl.

5. Compound according to claim 1, wherein $R^6$ and $R^7$ are —$OCH_3$ or -$^{tert}$Bu.

6. Compound according to claim 1, wherein $R^1$, $R^2$, $R^3$, $R^4$ are selected from —H, —($C_1$-$C_{12}$)-alkyl.

7. Compound according to claim 1, wherein $R^1$, $R^2$, $R^3$, $R^4$ are —H or -$^{tert}$Bu.

8. Compound according to claim 1, wherein the compound has one of the structures (1) to (6):

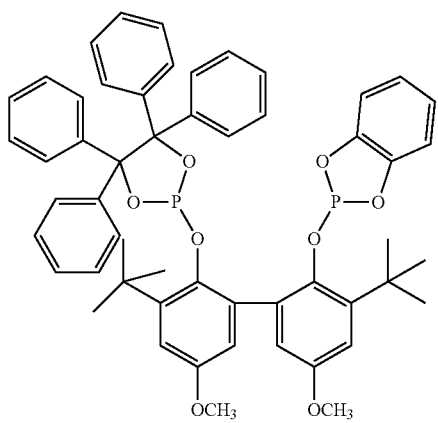

1

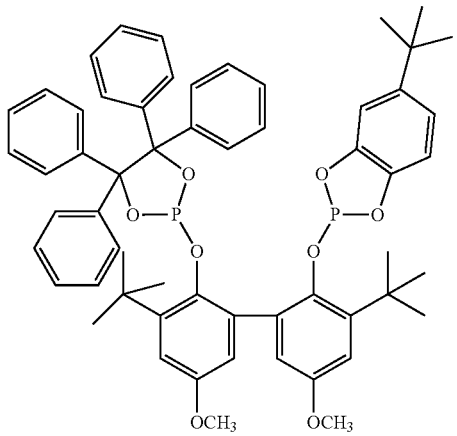

2

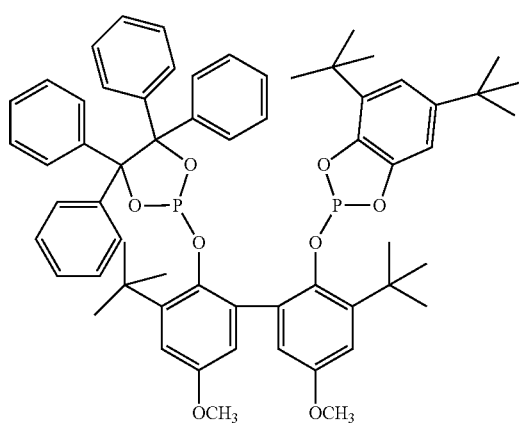

3

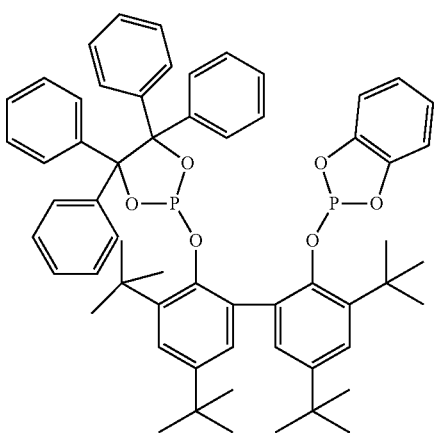

4

-continued

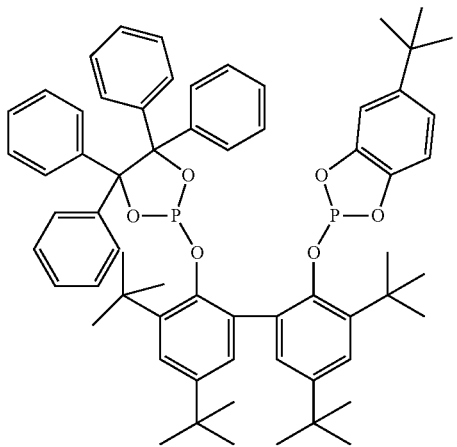

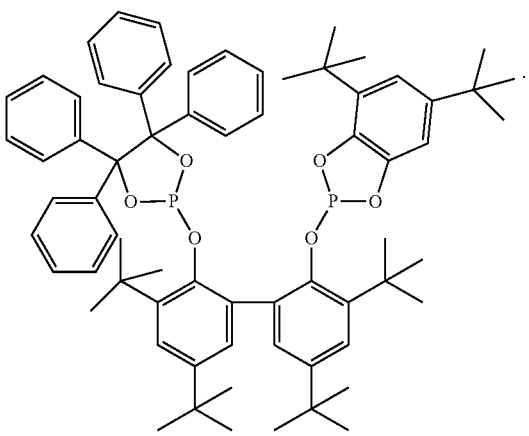

9. Process comprising the process steps of:
   a) initially charging an ethylenically unsaturated compound;
   b) adding a compound according to claim 1 and a substance comprising Rh;
   c) feeding in $H_2$ and CO,
   d) heating the reaction mixture from a) to c), with conversion of the olefin to an aldehyde.

10. Process according to claim 9,
    wherein the ethylenically unsaturated compound in process step a) is selected from: ethene, propene, 1-butene, cis- and/or trans-2-butene, isobutene, 1,3-butadiene, 1-pentene, cis- and/or trans-2-pentene, 2-methyl-1-butene, 3-methyl-1-butene, 2-methyl-2-butene, hexene, tetramethylethylene, heptene, 1-octene, 2-octene, di-n-butene, or mixtures thereof.

11. Process according to claim 9,
    wherein the substance comprising Rh is selected from: Rh(acac)(CO)$_2$, [(acac)Rh(COD)] (Umicore, acac=acetylacetonate anion; COD=1,5-cyclooctadiene), Rh$_4$CO$_{12}$.

12. Process according to claim 9,
    wherein CO is fed in in process step c) at a pressure in the range from 1 to 6 MPa (10 to 60 bar).

13. Process according to claim 9,
    wherein the reaction mixture is heated in process step d) to a temperature in the range from 80° C. to 160° C.

* * * * *